(12) United States Patent
Bar-El et al.

(10) Patent No.: US 11,571,517 B2
(45) Date of Patent: Feb. 7, 2023

(54) INJECTOR DELAYED CARTRIDGE PIERCING MECHANISM

(71) Applicant: West Pharma. Services IL, Ltd., Ra'anana (IL)

(72) Inventors: Yossi Bar-El, Beit Arye (IL); Gil Yigal, Gan Yavne (IL); Reuven Y. Filman, Tel Mond (IL)

(73) Assignee: West Pharma. Services IL, Ltd., Ra'anana (IL)

( * ) Notice: Subject to any disclaimer, the term of this patent is extended or adjusted under 35 U.S.C. 154(b) by 398 days.

(21) Appl. No.: 16/637,077

(22) PCT Filed: Aug. 2, 2018

(86) PCT No.: PCT/US2018/044993
§ 371 (c)(1),
(2) Date: Feb. 6, 2020

(87) PCT Pub. No.: WO2019/032374
PCT Pub. Date: Feb. 14, 2019

(65) Prior Publication Data
US 2020/0238012 A1 Jul. 30, 2020

Related U.S. Application Data

(60) Provisional application No. 62/543,725, filed on Aug. 10, 2017.

(51) Int. Cl.
*A61M 5/24* (2006.01)
*A61M 5/142* (2006.01)
(Continued)

(52) U.S. Cl.
CPC ...... *A61M 5/2459* (2013.01); *A61M 5/14248* (2013.01); *A61M 5/46* (2013.01);
(Continued)

(58) Field of Classification Search
CPC .. A61M 5/2459; A61M 5/14248; A61M 5/46; A61M 2005/14252;
(Continued)

(56) References Cited

U.S. PATENT DOCUMENTS 11,207,465 B2 * 12/2021 Bar-El ................ A61M 5/2053
2011/0066131 A1    3/2011 Cabiri
(Continued)

FOREIGN PATENT DOCUMENTS

| CA | 2990453 A1 | 1/2017 |
| CN | 101027094 A | 8/2007 |

(Continued)

OTHER PUBLICATIONS

Int'l Search Report and Written Opinion dated Oct. 25, 2018 in Int'l Application No. PCT/US2018/044993.
(Continued)

*Primary Examiner* — Lauren P Farrar
*Assistant Examiner* — Hamza A Darb
(74) *Attorney, Agent, or Firm* — Blank Rome LLP (57) ABSTRACT

An injector includes an injector housing, an activation button assembly translatable from an unactuated position to an actuated position and a cartridge door movably mounted to the injector housing between an open position and a closed position. A deflectable interference member has a resting position configured to limit an insertion depth of a cartridge into an interior channel of the cartridge door to a sealed position, wherein the cartridge piercing needle does not fully penetrate a pierceable septum of the cartridge. Movement of the activation button assembly from the unactuated position to the actuated position thereof, in the closed position of the cartridge door, deflects the interference element out of the resting position thereof, thereby enabling further advancement of the cartridge into the interior chan- (Continued)

nel of the cartridge door to an unsealed position, wherein the cartridge piercing needle fully penetrates the pierceable septum.

20 Claims, 8 Drawing Sheets

(51) Int. Cl.
    *A61M 5/46*     (2006.01)
    *A61M 5/20*     (2006.01)

(52) U.S. Cl.
    CPC ............ *A61M 2005/14252* (2013.01); *A61M 2005/208* (2013.01)

(58) Field of Classification Search
    CPC ...... A61M 2005/208; A61M 2005/247; A61M 2005/2496; A61M 2005/31588; A61M 5/14566; A61M 2005/2414; A61M 5/2455; A61M 5/24
    See application file for complete search history.

(56) References Cited

U.S. PATENT DOCUMENTS

| | | | |
|---|---|---|---|
| 2015/0320990 A1* | 11/2015 | Burton | A61M 5/1454 604/173 |
| 2016/0346478 A1 | 12/2016 | Bar-El et al. | |
| 2018/0154081 A1 | 6/2018 | Bar-El et al. | |

FOREIGN PATENT DOCUMENTS

| | | | |
|---|---|---|---|
| CN | 102271735 | A | 12/2011 |
| CN | 102497909 | A | 6/2012 |
| CN | 103118723 | A | 5/2013 |
| CN | 103269730 | A | 8/2013 |
| CN | 103687636 | A | 3/2014 |
| CN | 104321093 | A | 1/2015 |
| CN | 104853787 | A | 8/2015 |
| CN | 104870049 | A | 8/2015 |
| CN | 105263562 | A | 1/2016 |
| CN | 106029128 | A | 10/2016 |
| EP | 2459251 | A2 | 6/2012 |
| GB | 2552340 | A | 1/2018 |
| JP | 2012-516737 | A | 7/2012 |
| JP | 4996811 | B2 | 8/2012 |
| JP | 2013-504405 | A | 2/2013 |
| JP | 2016-516553 | A | 6/2016 |
| WO | 2011/014704 | A2 | 2/2011 |
| WO | 2012032411 | A2 | 3/2012 |
| WO | 2016196934 | A1 | 12/2016 |
| WO | 2017041996 | A1 | 3/2017 |

OTHER PUBLICATIONS

Int'l Preliminary Reporton Patentability dated Oct. 28, 2019 issued in Int'l Application No. PCT/US2018/044993.

\* cited by examiner

INJECTOR DELAYED CARTRIDGE PIERCING MECHANISM

CROSS-REFERENCE TO RELATED APPLICATIONS

This application is a Section 371 of International Application No. PCT/US2018/044993, filed Aug. 2, 2018, which was published in the English language on Feb. 14, 2019, under International Publication No. WO 2019/032374 A1, which claims the benefit of priority under 35 U.S.C. § 119(e) to U.S. Provisional Patent Application No. 62/543,725, titled "Piercing Preventing During Cartridge Loading", filed on Aug. 10, 2017, the entire contents of each of which are incorporated herein by reference in their entirety.

BACKGROUND OF THE DISCLOSURE

The present disclosure is generally directed to a cartridge loaded injector, and, more particularly, to a cartridge loaded injector configured to maintain a cartridge loaded therein in a sealed state until the device is activated for use.

An injector, such as, for example, a drug injector, is typically loaded with a cartridge containing therein a substance to be dispensed. The cartridge may be pre-loaded prior to delivery to a user, or, alternatively, the cartridge may be loaded by the user prior to use. Generally, the cartridge is sealed prior to loading, i.e., insertion, into the injector and unsealed during loading into the injector to place the substance within the cartridge in fluid communication with an injection needle of the injector.

One drawback of such a sequence is that the loaded cartridge may be left in an unsealed state for an excessive period of time prior to device activation, i.e., injection of the substance into the user. The unsealed cartridge is susceptible to leakage and/or contamination, rendering at least the cartridge unsuitable for use. Alternatively, the substance within the unsealed cartridge may flow into the fluid pathway connecting to the injection needle and dry or solidify prior to device activation, thereby potentially obstructing the fluid pathway and rendering the injector unusable. Moreover, once a cartridge is unsealed, it cannot be re-used. Therefore, if a user mistakenly loads the cartridge into the injector prematurely, or, if the injection is otherwise not performed, e.g., device malfunction, the unsealed cartridge is lost.

Therefore, it would be advantageous to manufacture an injector configured to maintain a cartridge loaded therein in a sealed state until the device is activated for use.

BRIEF SUMMARY OF THE DISCLOSURE

Briefly stated, one aspect of the present disclosure is directed to an injector configured to receive therein a cartridge containing a substance to be dispensed, the cartridge having an opening sealed by a pierceable septum. The injector includes an injector housing and an activation button assembly movably mounted to the injector housing, the activation button assembly being translatable from an unactuated position to an actuated position. An injection needle is translatable between a retracted position, wherein at least a tip of the injection needle is contained within the injector housing, and an injection position, wherein at least the tip of the injection needle protrudes from the injector housing. A cartridge door is movably mounted to the injector housing between an open position and a closed position. The cartridge door includes an open end, an interior channel configured to receive the cartridge therein, and a cartridge piercing needle mounted within the interior channel and fluidly connected with the injection needle. The cartridge piercing needle is configured to fully penetrate the pierceable septum of the cartridge to fluidly connect the substance within the cartridge with the injection needle. A deflectable interference member has a resting position configured to limit an insertion depth of the cartridge into the interior channel of the cartridge door to a sealed position, wherein the cartridge piercing needle does not fully penetrate the pierceable septum. The cartridge door is movable to the closed position thereof in the sealed position of the cartridge, and movement of the activation button assembly from the unactuated position to the actuated position thereof, in the closed position of the cartridge door, deflects the interference element out of the resting position thereof, thereby enabling further advancement of the cartridge into the interior channel of the cartridge door to an unsealed position, wherein the cartridge piercing needle fully penetrates the pierceable septum.

Another aspect of the present disclosure is directed to an injector having an injector housing and an injection needle translatable between a retracted position, wherein at least a tip of the injection needle is contained within the injector housing, and an injection position, wherein at least the tip of the injection needle protrudes from the injector housing. An activation button assembly is movably mounted to the injector housing and operatively connected to the injection needle, the activation button assembly being translatable from an unactuated position to an actuated position to drive the injection needle from the retracted position thereof to the injection position thereof. A cartridge door is movably mounted to the injector housing between an open position and a closed position. The cartridge door includes an open end, an interior channel having a cartridge mounted therein, the cartridge containing a substance to be dispensed and having an opening at a front end of the cartridge sealed by a pierceable septum and a flange at a rear end thereof, and a cartridge piercing needle mounted within the interior channel and fluidly connected with the injection needle. The cartridge piercing needle is configured to fully penetrate the pierceable septum of the cartridge to fluidly connect the substance within the cartridge with the injection needle. A deflectable interference member engages the rear end flange of the cartridge in a resting position of the interference member, thereby limiting an insertion depth of the cartridge into the interior channel of the cartridge door to a sealed position, wherein the cartridge piercing needle does not fully penetrate the pierceable septum. The cartridge door is movable to the closed position thereof in the sealed position of the cartridge, and movement of the activation button assembly from the unactuated position to the actuated position thereof, in the closed position of the cartridge door, deflects the interference element out of engagement with the rear end flange of the cartridge, thereby enabling further advancement of the cartridge into the interior channel of the cartridge door to an unsealed position, wherein the cartridge piercing needle fully penetrates the pierceable septum.

BRIEF DESCRIPTION OF THE DRAWINGS

The following detailed description of aspects of the disclosure will be better understood when read in conjunction with the appended drawings. It should be understood, however, that the invention is not limited to the precise arrangements and instrumentalities shown. In the drawings.

DETAILED DESCRIPTION OF THE DISCLOSURE

Certain terminology is used in the following description for convenience only and is not limiting. The words "lower," "bottom," "upper" and "top" designate directions in the drawings to which reference is made. The words "inwardly," "outwardly," "upwardly" and "downwardly" refer to directions toward and away from, respectively, the geometric center of the injector, and designated parts thereof, in accordance with the present disclosure. Unless specifically set forth herein, the terms "a," "an" and "the" are not limited to one element, but instead should be read as meaning "at least one." The terminology includes the words noted above, derivatives thereof and words of similar import.

It should also be understood that the terms "about," "approximately," "generally," "substantially" and like terms, used herein when referring to a dimension or characteristic of a component of the invention, indicate that the described dimension/characteristic is not a strict boundary or parameter and does not exclude minor variations therefrom that are functionally similar. At a minimum, such references that include a numerical parameter would include variations that, using mathematical and industrial principles accepted in the art (e.g., rounding, measurement or other systematic errors, manufacturing tolerances, etc.), would not vary the least significant digit.

Referring to the drawings in detail, wherein like numerals indicate like elements throughout, there is shown in FIGS. 1-8 an injector, generally designated 10, in accordance with an embodiment of the present disclosure. In the illustrated embodiment, the injector 10 takes the form of a wearable injector (patch injector), such as, for example, without limitation, a wearable drug injector, but the disclosure is not so limited. As should be understood by those of ordinary skill in the art, the injector 10 generally includes a housing 12 having a first surface 14 configured to contact a skin surface of a user (not shown), e.g., a patient, the first surface 14 having an opening 14a therein. In the illustrated embodiment, the first surface 14 defines a base surface of the injector housing 12, but the disclosure is not so limited. The housing 12 also includes a second surface 16 opposing the first surface 14. In the illustrated embodiment, the second surface 16 defines a top, external surface of the injector housing 12, but the disclosure is not so limited.

Figure 1:
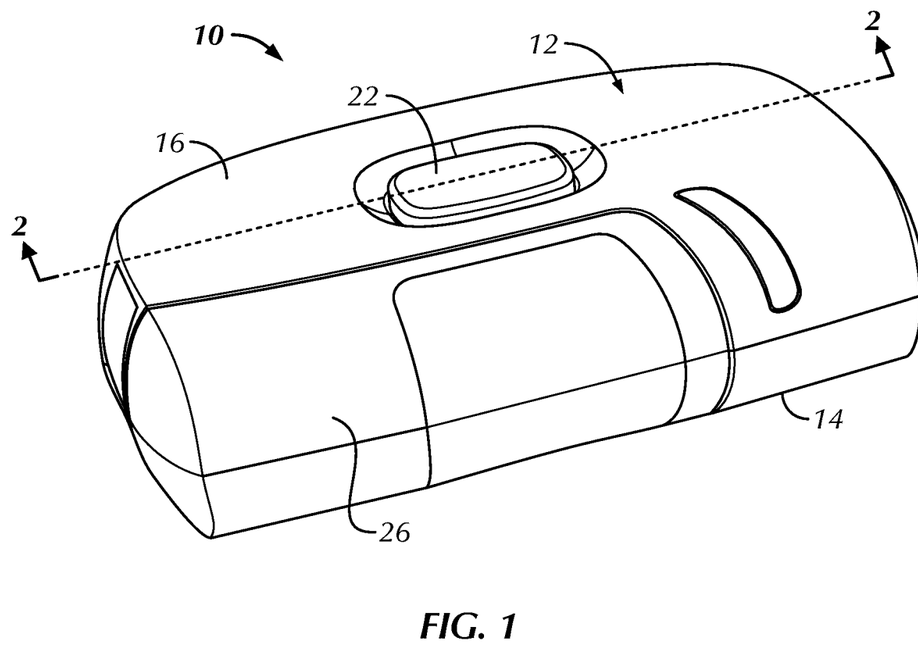
FIG. 1 is a top and front perspective view of a wearable injector, in accordance with an embodiment of the present disclosure.
Figure 2:
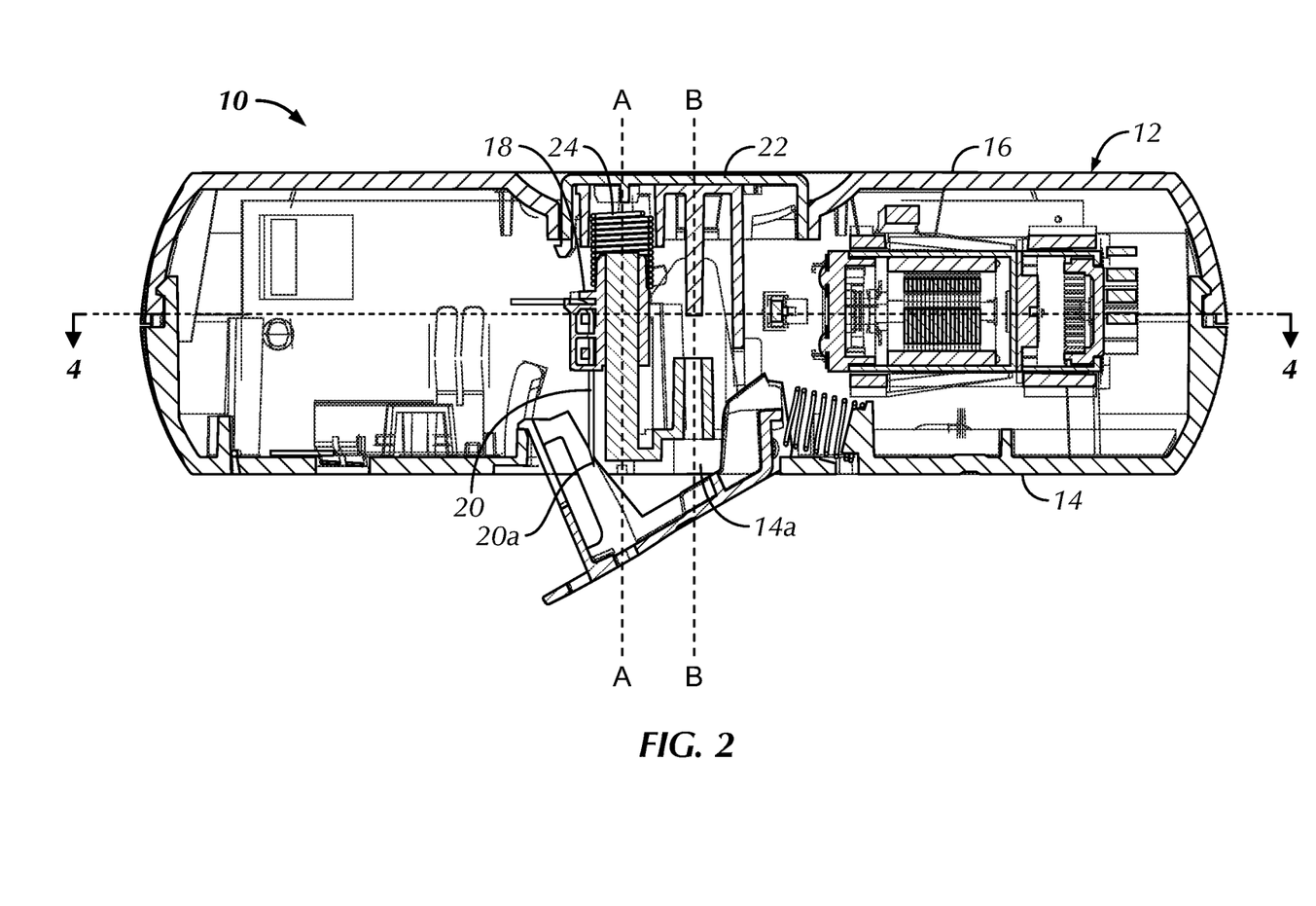
FIG. 2 is a cross-sectional view of the injector of FIG. 1, taken along the sectional line 2-2 of FIG. 1, with an activation button assembly in an unactuated position thereof and an injection needle in a retracted position thereof.
Figure 3:
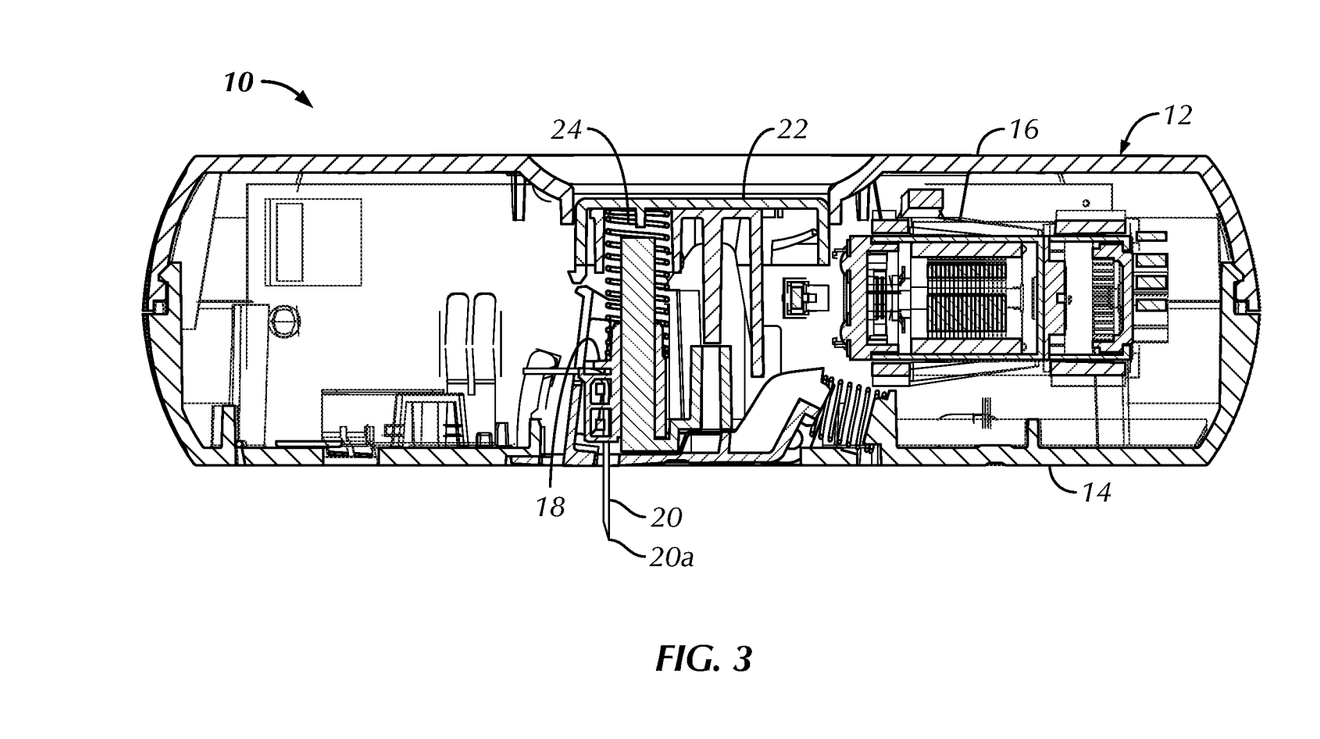
FIG. 3 is a cross-sectional view of the injector of FIG. 1, taken along the sectional line 2-2 of FIG. 1, with the activation button assembly in an actuated position thereof and the injection needle in an injection position thereof.
Figure 4:
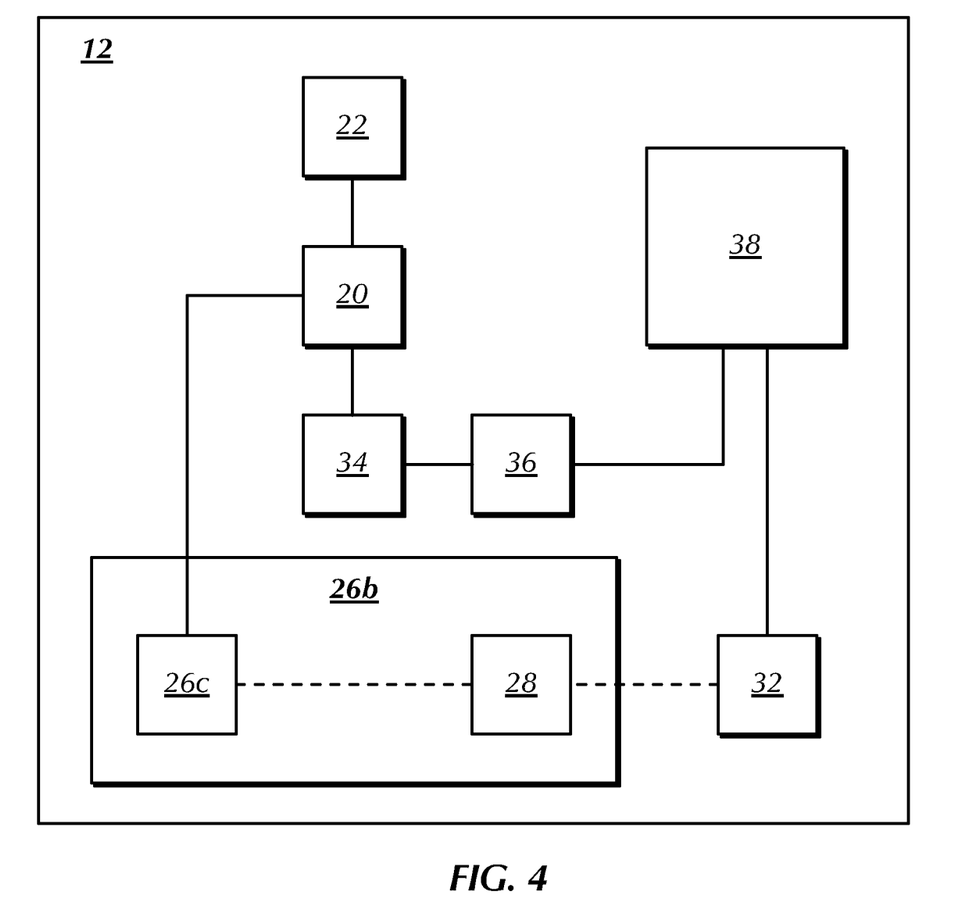
FIG. 4 is a schematic illustration of the operative connection between different components of the injector of FIG. 1, wherein the dotted lines illustrate an operative connection initiated upon injector activation.

As shown in FIGS. 2-3, a needle hub 18, constructed, for example, from a polymeric or metal material, combinations thereof, or the like, is movably mounted within the injector housing 12 and an injection needle 20 is supported by the movable needle hub 18 in a manner well understood by those of ordinary skill in the art. In the illustrated embodiment, the needle hub 18 and the injection needle 20 are axially translatable along a needle axis A (FIG. 2) extending substantially perpendicularly to the first surface 14, between a retracted position (FIG. 2), wherein at least a tip 20a of the injection needle 20 is contained within the injector housing 12, and an injection position (FIG. 3), wherein at least the tip 20a of the injection needle 20 protrudes from the injector housing 12 through the opening 14a. As should be understood by those of ordinary skill in the art, however, the needle axis A may be positioned at angles other than 90° relative to the first surface 14. As also should be understood, the injection needle 20 may be movably mounted within the injector housing 12 via other mechanisms than the needle hub 18.

A depressible activation button assembly 22, constructed, for example, from a polymeric or metal material, combinations thereof, or the like, is movably mounted to the injector housing 12 and operatively connected to the injection needle 20. The activation button assembly 22 is translatable, i.e., depressible, along a button axis B (FIG. 2) from an unactuated position (FIGS. 1, 2) to an actuated position (FIG. 3) in a manner well understood by those of ordinary skill in the art, to activate the injector 10. In the illustrated embodiment, the button axis B is parallel to the needle axis A, but the disclosure is not so limited. Activation of the injector 10 includes, for example, driving the injection needle 20 from the retraction position to the injection position thereof to perform an injection.

As shown in FIGS. 2-3, a biasing member 24 is operatively connected with the activation button assembly 22 and the injection needle 20, but the disclosure is not so limited. As one alternative example, the biasing member 24 may be connected with the second surface 16 and the injection needle 20. The biasing member 24 is stabilized in a stored energy state in the unactuated position of the activation button assembly 22 (FIG. 2) and released into an energy releasing state, when the activation button assembly 22 is translated into the actuated position thereof (FIG. 3), to drive the injection needle 20 along the needle axis A from the retracted position thereof to the injection position thereof. As should be understood by those of ordinary skill in the art, the stored energy state of the biasing member 24 is a state in which the biasing member 24 stores at least some potential energy. The energy releasing state of the biasing member 24 is a state of the biasing member 24 in which the biasing member 24 releases at least some of the previously stored potential energy from the stored energy state.

In the illustrated embodiment, the biasing member 24 takes the form of a coil spring mounted between the needle hub 18 and the activation button assembly 22, i.e., the spring 24 abuts the activation button assembly 22 at one end and abuts the needle hub 18 at an opposing end. In the energy storing state, the coil spring 24 is at least partially compressed. In the energy releasing state, the coil spring 24 expands (relative to the at least partially compressed energy storing state) to drive the needle hub 18 and the injection needle 20 into the injection position thereof. As should be understood by those of ordinary skill in the art, however, the biasing member 24 may alternatively take the form of other members capable of storing and releasing energy. Non-limiting examples include other springs (e.g., torsion or leaf springs), elastic bands, and the like. Alternatively, the biasing member 24 may take the form of an actuator configured to apply a translational force onto the injection needle 20 when the activation button assembly 22 is depressed into the actuated position thereof.

The injector 10 further includes a cartridge door 26 defining an open end 26a for receiving, e.g., slidably, a cartridge 28 (FIGS. 5-8) therethrough, and an interior channel 26b to receive the cartridge 28 therein. The interior channel 26b may be sized and shaped to receive and stabilize the cartridge 28 therein. Alternatively, the interior channel 26b may include a cartridge cradle, a cartridge track, individual stabilizing members, combinations thereof, or the like (not shown) to receive and stabilize the cartridge 28 in the interior channel 26b.

As should be understood, the cartridge 28 includes a reservoir 28a having a first opening 28b and a second opening 28c. The reservoir 28a contains a substance (not shown), e.g., medicament, to be dispensed from the injector 10 through the injection needle 20. In the illustrated embodiment the first opening 28b of the cartridge 28 is a distal opening, but the location thereof is not so limited. The first opening 28b is sealed by a pierceable septum 29 in a manner well understood by those of ordinary skill in the art. In the illustrated embodiment the second opening 28c of the cartridge 28 is a proximal opening, but the location thereof is also not so limited. The second opening 28c is sealed by a piston 27 movably mounted within the reservoir 28a and sealingly engaged with an interior sidewall of the reservoir 28a in a manner well understood by those of ordinary skill in the art. The substance within the reservoir 28a is sealed between the piston 27 and the septum 29.

The second opening 28c of the cartridge 28 includes a flange 28d laterally extending therefrom. In the illustrated embodiment, the flange 28d is an annular flange, i.e., laterally extending from the entire perimeter of the second opening 28c, but the disclosure is not so limited. As should be understood, the flange 28d may extend from only a portion of the perimeter (less than the entirety thereof) of the second opening 28c, and may also laterally extend from elsewhere along the length of the cartridge 28. As shown, the outer periphery of the flange 28d of the cartridge 28 defines a largest outer perimeter of the cartridge 28. In the illustrated embodiment, the shape of the cartridge 28 is defined by a series of generally cylindrical portions, e.g., a cylindrical neck, body and flange, and the flange 28d of the cartridge 28 defines a largest outer circumference of the cartridge 28 (but the disclosure is not so limited).

Figure 5:
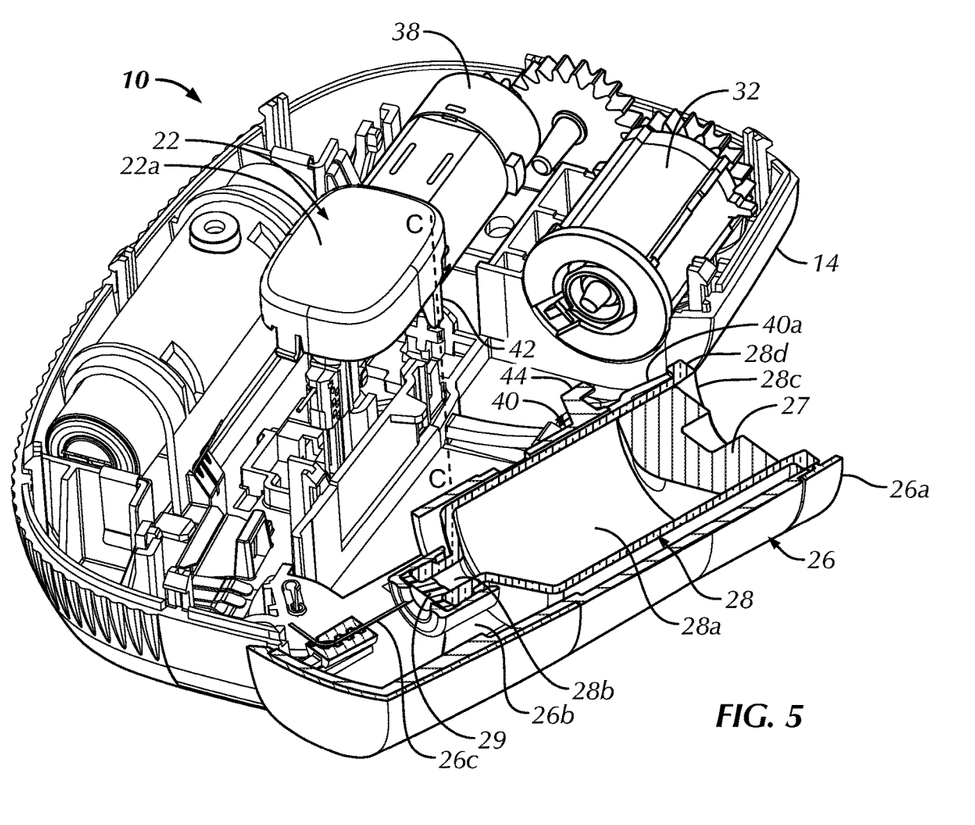
FIG. 5 is a top, front and left side perspective view of the injector of FIG. 1 having a top cover of the injector removed, with an activation button assembly in an unactuated position thereof, a cartridge door in an open position thereof and a sealed cartridge inserted therein.

The cartridge door 26 is movably mounted to the injector housing 12, between an open position (e.g., FIG. 5) and a closed position (FIGS. 1, 6-8). In the closed position, the interior channel 26b is inaccessible from outside of the injector housing 12. For example, in the illustrated embodiment, the open end 26a of the cartridge door 26 is sufficiently covered by a portion of the injector housing 12 such that access to the interior channel 26b is prevented. In the open position, the open end 26a of the cartridge door 26 is at least partially uncovered, and the interior channel 26b is at least partially accessible from the open end 26a. In a fully open position of the cartridge door 26, as shown in FIG. 5, the open end 26a of the cartridge door 26 is sufficiently uncovered to permit insertion of the cartridge 28 therethrough and into the interior channel 26b.

In the illustrated embodiment, the cartridge door 26 is pivotably attached to the injector housing 12, e.g., via pin connection 30, proximate a closed, distal end of the interior channel 26b, opposite the open end 26a, but the disclosure is not so limited. As shown in FIG. 5, the cartridge door 26 is pivoted away from the injector housing 12 in the open position, whereby the interior channel 26b is accessible from the open end 26a of the cartridge door 26. Other non-limiting examples of a cartridge door 26 movably mounted to an injector housing 12 are described in U.S. Patent Application Publication No. 2018/0154081, entitled, "Cartridge Insertion For Drug Delivery Device," the entire contents of which are incorporated by reference herein.

The cartridge door 26 further includes a cartridge piercing needle 26c mounted within the interior channel 26b. As shown schematically in FIG. 4, the cartridge piercing needle 26c is fluidly connected to the injection needle 20 in a manner well understood by those of ordinary skill in the art, e.g., via a flexible tube (not shown) extending from the piercing needle 26c to the injection needle 20. In the illustrated embodiment, the cartridge piercing needle 26c is positioned proximate the closed, distal end of the interior channel 26b, opposite the open end 26a. The cartridge piercing needle 26c extends inwardly into the interior channel 26b and terminates at a tip of the needle 26c, positioned to face and align with the pierceable septum 29 of the cartridge 28 when the cartridge 28 is inserted into the cartridge door 26. The cartridge piercing needle 26c is configured to fully penetrate the pierceable septum 29 of the cartridge 28 to fluidly connect the substance within the cartridge 28 with the injection needle 20 when the injector 10 is activated, as will be described in further detail below.

The injector 10 further includes a driving assembly 32 (FIGS. 5, 6 and 8 and schematically in FIG. 4) positioned and configured to engage the piston 27 (through the open end 26a of the cartridge door 26 and the second opening 28c of the cartridge 28) subsequent to device activation to expel the substance out of the cartridge 28, as will be explained in further detail below. In one non-limiting example, the driving assembly 32 may take the form of a telescopic driving assembly, i.e., a plurality of threaded shafts threadably connected to one another in a telescopic manner whereby rotation of at least one of the shafts linearly translates at least another of the shafts, but the disclosure is not so limited. One example of a telescoping driving assembly is described in U.S. Patent Application Publication No. 2016/0346478, entitled "Linear Rotation Stabilizer For A Telescoping Syringe Stopper Driverdriving Assembly", the entire contents of which are incorporated by reference herein.

The driving assembly 32 is operatively engaged with the activation button assembly 22. In one non-limiting example, and as shown schematically in FIG. 4, the injector 10 may include a sensor 34, e.g., an optical position sensor, configured to detect movement of the injection needle 20 (in a manner well understood by those of ordinary skill in the art) from the retracted position thereof into the injection position thereof, which is generated (as previously explained) by movement of the activation button assembly 22 from the unactuated position thereof to the actuated position thereof. Alternatively, or additionally, the sensor 34 may be configured to detect movement of the activation button assembly 22 itself from the unactuated position thereof to the actuated position thereof. The sensor 34 may be connected to a control assembly 36, e.g., a processor, and configured to transmit an output signal thereto (in a manner well understood by those of ordinary skill in the art) indicative of the injection needle 20 becoming positioned in the injection position thereof. In response, the control assembly 36 may be configured to activate an actuator 38 (in a manner well understood by those of ordinary skill in the art). Non-limiting examples of an actuator 38 include a motor, a spring actuator, a gaseous actuator, a chemical actuator, an electrical actuator, an electromechanical actuator, combinations thereof, or the like. Upon activation, the actuator 38 is configured to drive the driving assembly 32 (in a manner well understood by those of ordinary skill in the art), e.g., via a series of interconnected rotatable gears, from an initial position, unengaged with the piston 27, into engagement with the piston 27.

The injector 10 further includes a deflectable interference member 40 having a resting position (FIGS. 5, 6) in which the interference member 40 limits an insertion depth of the cartridge 28 into the interior channel 26b of the cartridge door 26. When in the resting position thereof, the interference member 40 permits insertion of the cartridge 28 into the interior channel 26b of the door 26 to a sealed position wherein the cartridge 28 is loaded, but remains sealed. That is, the interference member 40 prevents the cartridge 28 from reaching a position wherein the piercing needle 26c fully penetrates the pierceable septum 29, thereby fluidly connecting the substance within the cartridge 28 with the injection needle 20. In the illustrated embodiment, the cartridge piercing needle 26c does not engage the septum 29 in the sealed position of the cartridge 28. Alternatively, the cartridge piercing needle 26c may partially penetrate the septum 29 in the sealed position of the cartridge 28, without fully penetrating through the septum 29. As shown best in FIG. 5, the interior channel 26b of the cartridge door 26 defines a length greater than a length of the cartridge 28. Accordingly, in the resting position of the interference member 40, the cartridge 28 is sufficiently insertable into the interior channel 26b of the cartridge door 26 to permit movement of the cartridge door 26 into the closed position thereof, while remaining in the sealed state thereof (FIGS. 5 and 6).

In the illustrated embodiment, the deflectable interference member 40 takes the form of a cantilevered arm/finger defining a deflectable portion of the sidewall of the cartridge door 26. That is, the cantilevered arm 40 is integrally formed with the sidewall of the cartridge door 26, e.g., co-molded therewith, having a first end connected to the cartridge door 26 and extending (as a deflectable portion of the sidewall) to a second, free end 40a proximate the open end 26a of the cartridge door 26. The disclosure is not so limited, however, and the cantilevered arm 40 may be formed separately or individually and connected or attached, directly or indirectly to the cartridge door 26. Alternatively, the deflectable interference member 40 may take other forms capable of performing the function of the interference member 40 disclosed herein, such as, for example, without limitation, a spring actuated deflectable interference member. The cartridge door 26 and the deflectable interference member 40 may each be constructed, for example, from a polymeric or metal material, combinations thereof, or the like.

Figure 6:
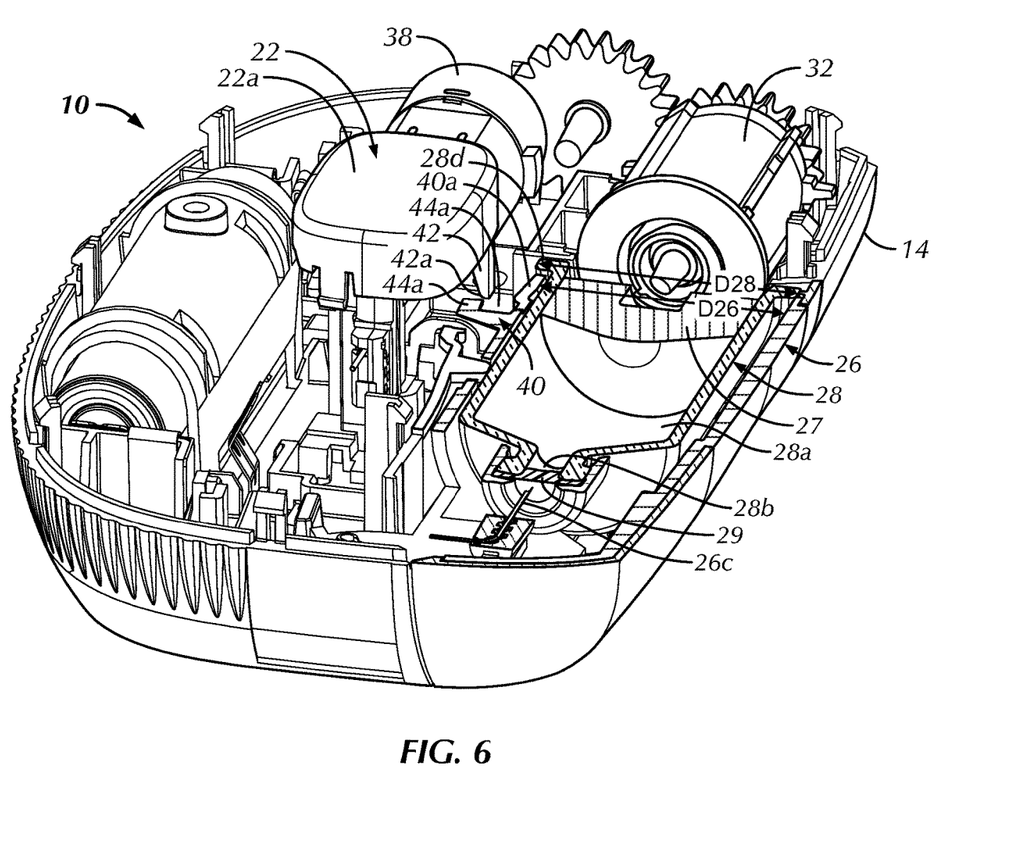
FIG. 6 is a top, front and left side perspective view of the injector of FIG. 1 having the top cover of the injector removed, with the activation button assembly in the unactuated position thereof, the cartridge door in a closed position thereof and the sealed cartridge inserted therein.

As shown in FIGS. 5 and 6, an internal diameter D26 of the cartridge door 26 at the second, free end 40a of the cantilevered arm 40 is smaller than an outer diameter D28 of the cartridge 28 at the rear flange 28d thereof, when the cantilevered arm 40 is in the resting position thereof. As previously explained, the rear flange 28d defines a largest outer circumference of the cartridge 28. Accordingly, the inner perimeter of the cartridge door 26 at the second, free end 40a of the cantilevered arm 40 is smaller than an outer perimeter of the cartridge 28 at the rear flange 28d thereof in the resting position of the cantilevered arm 40. When the cartridge door 26 is opened to insert a cartridge therein, the cantilevered arm 40 is positioned in the resting position thereof. Thus, the second, free end 40a of the cantilevered arm 40 engages the rear flange 28d of the cartridge 28 during insertion of the cartridge 28 into the interior channel 26b of the cartridge door 26 and blocks further advancement of the cartridge 28 into the interior channel 26b. The cartridge door 26 and the piercing needle 26c are sized and dimensioned such that the piercing needle 26c does not fully penetrate the septum 29 of the cartridge 28 at the position of the cartridge 28 within the interior channel 26b when stopped by the second, free end 40a of the cantilevered arm 40.

As shown best in FIGS. 5-8, the activation button assembly 22 includes a post 42 extending therefrom. In the illustrated embodiment, the post 42 extends downwardly (i.e., parallel with button axis B) from a cover 22a of the activation button assembly 22, but the disclosure is not so limited. As shown best in FIGS. 6 and 7, the post 42 tapers to a terminal end thereof opposite from the cover 22a. The post 42 starts to taper at least partially along the length thereof. That is, the post 42 defines a tapered face 42a along at least a portion of the length of the post 42, resulting in a gradual thinning of the post 42 in a direction toward the terminal end (otherwise viewed as a gradual thickening of the post 42 from the terminal end thereof in a direction toward the cover 22a). As should be understood, the post 42 may taper along the entire length thereof or along a portion of the length thereof. The post 42 defines a post pathway C, parallel to the button axis B, along which the post 42 travels during movement of the activation button assembly 22 from the unactuated position to the actuated position.

Figure 7:
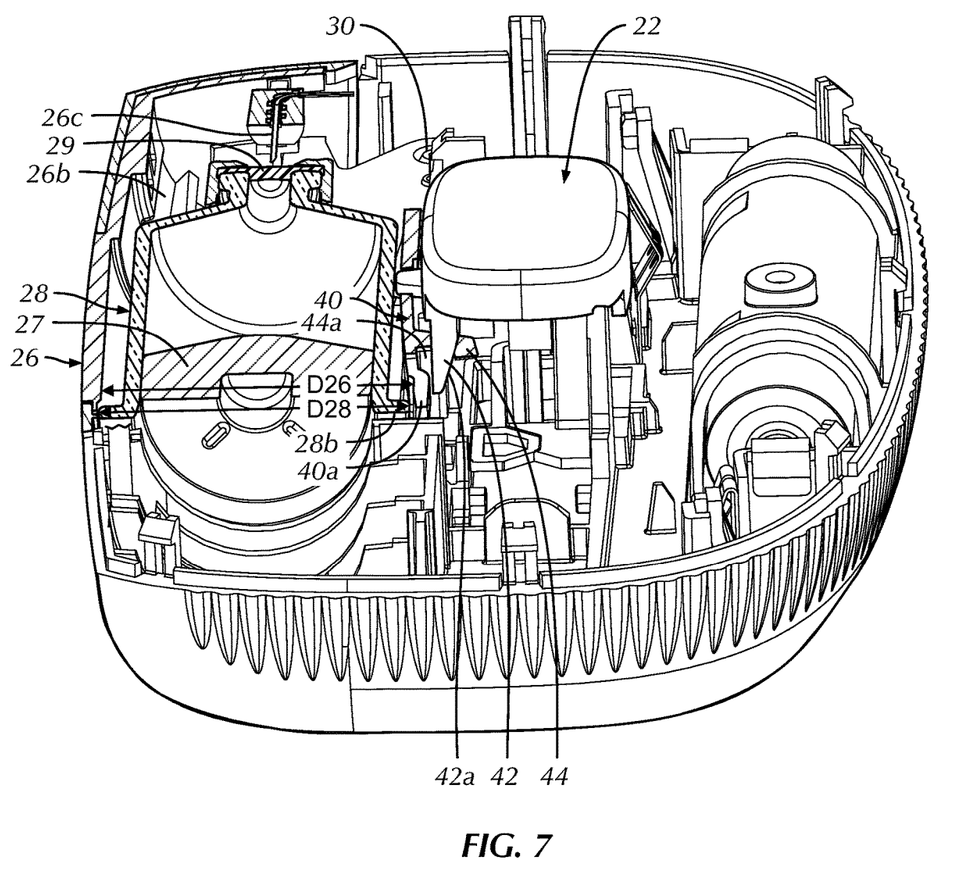
FIG. 7 is a top and right side perspective view of the injector of FIG. 1 having the top cover, a driving assembly and an actuator of the injector removed, with the cartridge door in the closed position thereof and the activation button assembly in an actuated position thereof, thereby deflecting an interference element limiting the insertion depth of the cartridge into the cartridge door.

The cantilevered arm 40 defines a hook-shaped tab 44 laterally extending from the sidewall of the cartridge door 26 toward the post pathway C. In the closed position of the cartridge door 26, the hook-shaped tab 44 extends through the post pathway C (FIG. 6). Accordingly, movement of the activation button assembly 22 from the unactuated position to the actuated position thereof, in the closed position of the cartridge door 26, engages the post 42 with the hook-shaped tab 44. The post 42 slides through the central aperture 44a of the hook-shaped tab 44 with the tapered face 42a of the post 42 facing toward the hooked end of the tab 44 and away from the cartridge door 26. As the tapered post 42 travels downwardly through the central aperture 44a of the tab 44, the increasing thickness of the post 42 (due to the reverse taper) engages and laterally translates the hooked end of the tab 44 (FIG. 7). The tapered face 42a of the post 42 is inclined from the terminal end thereof toward the cover 22a in a direction away from the cartridge door 26. Accordingly, the hooked end of the tab 44 is laterally translated away from the cartridge door 26, and, in turn, deflecting the cantilevered arm 40 away from the resting position thereof in a direction away from the cartridge door 26. As should be understood, the post 42 may be constructed to define a greater bending stiffness, i.e., resistance against bending deformation/deflection, than the cantilevered arm 40, such that engagement of the post 42 with the hook-shaped tab 44 results in deflection of the cantilevered arm 40. Such properties may be achieved via relative material properties, between the post 42 and the cantilevered arm 40, as well as relative dimensions between the post 42 and the cantilevered arm 40, or a combination thereof.

As shown in FIG. 7, the internal diameter D26 of the cartridge door 26 at the second, free end 40a of the cantilevered arm 40 is greater than the outer diameter D28 of the cartridge 28 at the rear flange 28d thereof, in the deflected position of the cantilevered arm 40. That is, the inner perimeter of the cartridge door 26 at the second, free end 40a of the cantilevered arm 40 is greater than an outer perimeter of the cartridge 28 at the rear flange 28d thereof in the deflected position of the cantilevered arm 40. As shown in FIG. 7, the second, free end of the cantilevered arm 40 clears the rear flange 28d of the cartridge 28. Thus, when the activation button 22 is depressed from the unactuated position to the actuated position thereof (with the cartridge door 26 in the closed position), deflecting the cantilevered arm 40 with the post 42, the cartridge 28 is unblocked and further advancement of the cartridge 28 into the interior channel 26b of the cartridge door 26 is enabled.

Figure 8:
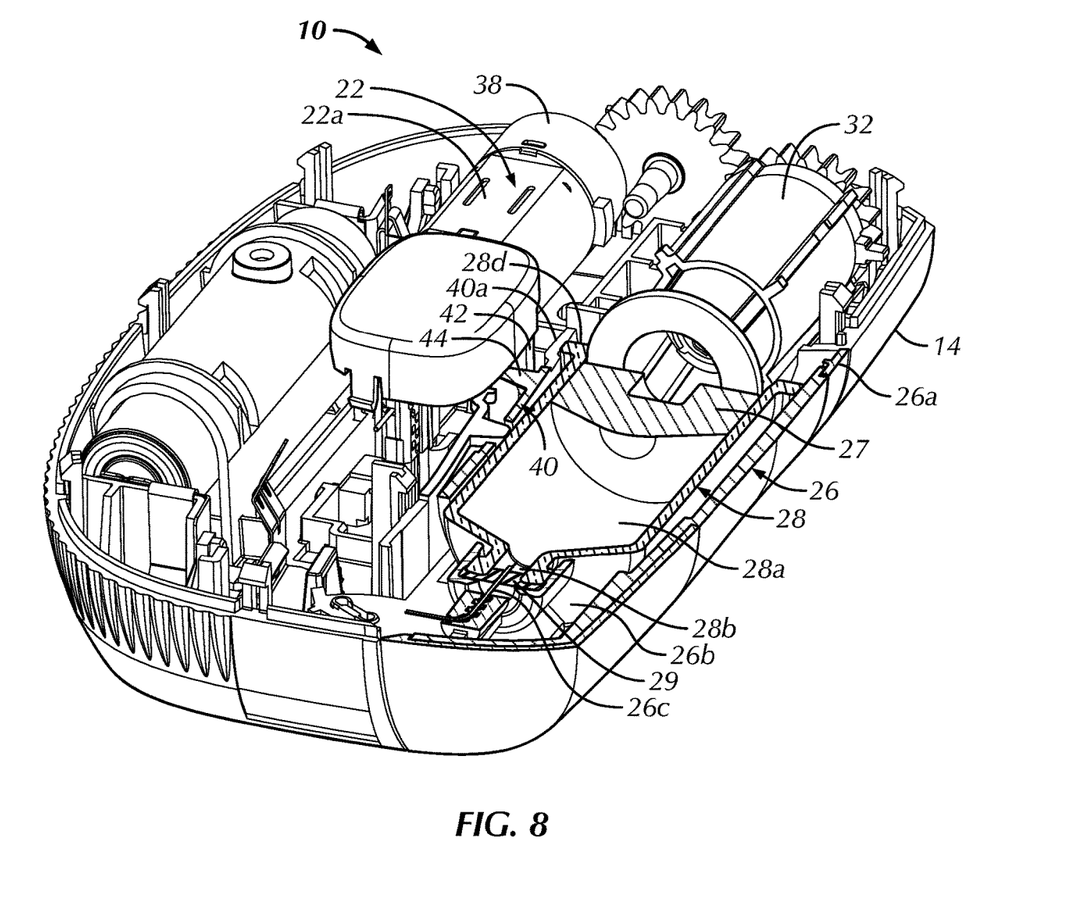
FIG. 8 is a top, front and left side perspective view of the injector of FIG. 1 having the top cover of the injector removed, with the cartridge door in the closed position thereof and the activation button assembly in the actuated position thereof, with the driving assembly advancing the cartridge further into the cartridge door into an unsealed position thereof.

In use, the cartridge door 26 is opened and the cartridge 28 is inserted into the interior channel 26b thereof, until the rear flange 28d of the cartridge 28 engages the second, free end 40a of the cantilevered arm 40 in the resting position of the cantilevered arm 40 (FIG. 5). Advantageously, the cartridge 28 remains sealed. The cartridge door 26 is thereafter moved into the closed position thereof, aligning the cartridge door 26 (and the cartridge 28 therein) with the driving assembly 32 secured within the injector housing 12. When ready for use, the activation button assembly 22 is translated from the unactuated position thereof to the actuation position, deflecting the cantilevered arm 40 away from the resting position thereof as previously explained and freeing the cartridge 28 for further advancement into the interior channel 26b of the cartridge door 26. As also previously explained, the activation button assembly 22 is operatively connected with the driving assembly 32, and movement of the activation button assembly 22 into the actuated position thereof also drives the driving assembly forward and into engagement with the piston 27 (FIG. 8). Upon initial contact between the driving assembly 32 and the piston 27, the cartridge 28 remains sealed. Thus the driving force of the driving assembly onto the piston 27 drives the entire cartridge 28 forward, whereby the septum 29 is fully penetrated by the piercing needle 26c and the cartridge 28 is unsealed.

In one embodiment, the cartridge 28 is driven forward until the cartridge 28 reaches a stop surface (not shown). For example, the stop surface may take the form of a step (not shown) laterally inwardly projecting from the inner sidewall of the cartridge door 26 and configured, e.g., positioned and dimensioned, to abut the rear flange 28d of the cartridge 28 upon full penetration of the septum 29 by the piercing needle 26c. The substance within the cartridge 28 therefore becomes fluidly connected with the injection needle 20 upon penetration of the septum 29 and further forward advancement of the cartridge 28 is stopped. Once the cartridge 28 is unsealed and stopped, further driving force of the driving assembly 32 applied to the piston 27 advances the piston forward through the reservoir 28a of the cartridge 28 and causing the substance within the reservoir 28a to flow through the piercing needle 26c, to the injection needle 20, and, to be dispensed out of the injection needle 20.

Advantageously, the cartridge 28 is preserved in a sealed state until the injector 10 is activated for use, as the interference element 40 blocks full insertion of the cartridge 28 until the activation button 22 is translated into the actuated position thereof. Accordingly, the injector 10 is not subjected to leakage, contamination or blockage of flow prior to injector activation. Moreover, if the injector 10 is damaged or the injection is otherwise not performed, e.g., an error occurs and is recognized between initial cartridge 28 loading and actuation of the activation button assembly 22, the cartridge 28 remains sealed and usable with another injector 10.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention, as set forth in the appended claims.

We claim:

1. An injector configured to receive a cartridge containing a substance to be dispensed, the cartridge having an opening sealed by a pierceable septum, the injector comprising:
    an injector housing;
    an activation button assembly movably mounted to the injector housing, the activation button assembly being translatable from an unactuated position to an actuated position;
    an injection needle translatable between a retracted position, where at least a tip of the injection needle is contained within the injector housing, and an injection position, where at least the tip of the injection needle protrudes from the injector housing;
    a cartridge door movably mounted to the injector housing between an open position and a closed position, the cartridge door comprising:
        an open end,
        an interior channel configured to receive the cartridge, and
        a cartridge piercing needle mounted within the interior channel and fluidly connected with the injection needle; and
    an interference member having a resting position configured to limit an insertion depth of the cartridge in the interior channel of the cartridge door to a sealed position, wherein the cartridge piercing needle does not fully penetrate the pierceable septum in the sealed position,
    wherein the cartridge door is movable to the closed position when the cartridge is in the sealed position, and
    wherein movement of the activation button assembly from the unactuated position to the actuated position, when the cartridge door is in the closed position, deflects the interference member out of the resting position, thereby enabling advancement of the cartridge in the interior channel of the cartridge door to an unsealed position, wherein the cartridge piercing needle fully penetrates the pierceable septum in the unsealed position to dispense the substance through the injection needle.

2. The injector of claim 1, further comprising a driving assembly engageable with the cartridge to expel the substance therefrom, the driving assembly being operatively engaged with the activation button assembly and being configured to drive the cartridge from the sealed position to the unsealed position upon movement of the activation button assembly from the unactuated position to the actuated position.

3. The injector of claim 1, wherein the interior channel defines a length greater than a length of the cartridge.

4. The injector of claim 1, wherein the interference member comprises a cantilevered arm.

5. The injector of claim 4, wherein the cantilevered arm defines a first end connected to the cartridge door and extends to a second, free end proximate the open end of the cartridge door.

6. The injector of claim 5, wherein the cartridge door comprises a sidewall, and the cantilevered arm defines a deflectable portion of the sidewall of the cartridge door.

7. The injector of claim 6, wherein the cantilevered arm is integrally formed with the sidewall of the cartridge door.

8. The injector of claim 6, wherein the sidewall of the cartridge door defines a first internal perimeter at the second, free end of the cantilevered arm when the cantilevered arm is in the resting position thereof, and the sidewall of the cartridge door defines a second internal perimeter at the second, free end of the cantilevered arm when the cantilevered arm is deflected from the resting position thereof, the first internal perimeter being smaller than a largest outer perimeter of the cartridge insertable into the interior channel, thereby limiting the insertion depth of the cartridge in the interior channel of the cartridge door, and the second internal perimeter being greater than the largest outer perimeter of the cartridge, thereby enabling advancement of the cartridge in the interior channel of the cartridge door.

9. The injector of claim 4, wherein the activation button assembly comprises a post extending therefrom to a terminal end having a tapered face, the post having a post pathway along which the post travels from the unactuated position of the activation button assembly to the actuated position of the activation button assembly, and wherein the cantilevered arm comprises a tab laterally extending therefrom toward the post pathway, the tab having a hooked end facing the tapered face of the post, wherein movement of the activation button assembly from the unactuated position to the actuated position, in the closed position of the cartridge door, engages the post with the tab, the tapered face engaging and laterally translating the hooked end, and, in turn, deflecting the cantilevered arm away from the resting position thereof.

10. The injector of claim 1, wherein the activation button assembly is operatively connected to the injection needle, whereby movement of the activation button assembly from the unactuated position to the actuated position thereof drives the injection needle from the retracted position to the injection position thereof.

11. The injector of claim 1, wherein the cartridge door is pivotably mounted to the injector housing at an end of the cartridge door opposite the open end thereof.

12. An injector comprising:
an injector housing;
an injection needle translatable between a retracted position, where at least a tip of the injection needle is contained within the injector housing, and an injection position, where at least the tip of the injection needle protrudes from the injector housing;
an activation button assembly movably mounted to the injector housing and operatively connected to the injection needle, the activation button assembly being translatable from an unactuated position to an actuated position to drive the injection needle from the retracted position to the injection position;
a cartridge door movably mounted to the injector housing between an open position and a closed position, the cartridge door comprising:
an open end,
an interior channel having a cartridge mounted therein, the cartridge containing a substance to be dispensed and having an opening at a front end of the cartridge and a flange at a rear end of the cartridge, and
a cartridge piercing needle mounted within the interior channel and fluidly connected with the injection needle; and
an interference member engaging the flange of the cartridge in a resting position of the interference member, thereby limiting an insertion depth of the cartridge in the interior channel of the cartridge door to a sealed position, wherein the cartridge piercing needle does not fully penetrate a pierceable septum in the sealed position;
wherein the cartridge door is movable to the closed position in the sealed position of the cartridge, and
wherein movement of the activation button assembly from the unactuated position to the actuated position, when the cartridge door is in the closed position, deflects the interference member out of engagement with the flange of the cartridge, thereby enabling advancement of the cartridge in the interior channel of the cartridge door to an unsealed position, wherein the cartridge piercing needle fully penetrates the pierceable septum in the unsealed position to dispense the substance through the injection needle.

13. The injector of claim 12, wherein the interference member comprises a cantilevered arm.

14. The injector of claim 13, wherein the cantilevered arm defines a first end connected to the cartridge door and extends to a second, free end proximate the open end of the cartridge door.

15. The injector of claim 14, wherein the cartridge door comprises a sidewall and the cantilevered arm defines a deflectable portion of the sidewall of the cartridge door.

16. The injector of claim 15, wherein the sidewall of the cartridge door defines a first internal perimeter at the second, free end of the cantilevered arm when the cantilevered arm is in the resting position thereof, and the sidewall of the cartridge door defines a second internal perimeter at the second, free end of the cantilevered arm when the cantilevered arm is deflected from the resting position thereof, the first internal perimeter being smaller than a perimeter of the rear end flange of the cartridge insertable into the interior channel, thereby limiting the insertion depth of the cartridge in the interior channel of the cartridge door, and the second internal perimeter being greater than the rear end flange perimeter of the cartridge, thereby enabling advancement of the cartridge in the interior channel of the cartridge door.

17. The injector of claim 13, wherein the activation button assembly comprises a post extending therefrom to a terminal end having a tapered face, the post having a post pathway along which the post travels from the unactuated position of the activation button assembly to the actuated position of the activation button assembly, and wherein the cantilevered arm comprises a tab laterally extending therefrom toward the post pathway, the tab having a hooked end facing the tapered face of the post, wherein movement of the activation button assembly from the unactuated position to the actuated position, in the closed position of the cartridge door, engages the post with the tab, the tapered face engaging and laterally translating the hooked end, and, in turn, deflecting the cantilevered arm away from the resting position thereof.

18. An injector configured to receive a cartridge containing a substance to be dispensed, the cartridge having an opening sealed by a pierceable septum, the injector comprising:
   an injector housing;
   an activation button assembly movably mounted to the injector housing, the activation button assembly being translatable from an unactuated position to an actuated position;
   an injection needle;
   a cartridge door movably mounted to the injector housing between an open position and a closed position, the cartridge door comprising:
      an interior channel configured to receive the cartridge, and
      a cartridge piercing needle fluidly connected with the injection needle; and
   an interference member having a position configured to limit an insertion depth of the cartridge in the interior channel of the cartridge door to a sealed position, wherein the cartridge piercing needle does not fully penetrate the pierceable septum in the sealed position,
   wherein the cartridge door is movable to the closed position when the cartridge is in the sealed position, and
   wherein movement of the activation button assembly from the unactuated position to the actuated position, when the cartridge door is in the closed position, moves the interference member out of the position, thereby enabling advancement of the cartridge in the interior channel of the cartridge door to an unsealed position, wherein the cartridge piercing needle fully penetrates the pierceable septum in the unsealed position to inject the substance through the injection needle.

19. The injector of claim 18, wherein the interior channel defines a length greater than a length of the cartridge.

20. The injector of claim 18, wherein the interference member comprises a cantilevered arm.

* * * * *